(12) United States Patent
George

(10) Patent No.: US 7,920,265 B1
(45) Date of Patent: Apr. 5, 2011

(54) APPARATUS AND METHOD FOR NOISE REDUCTION IN MODULATED OPTICAL REFLECTANCE METROLOGY SYSTEM

(75) Inventor: Alan George, San Jose, CA (US)

(73) Assignee: KLA-Tencor Corporation, San Jose, CA (US)

( * ) Notice: Subject to any disclaimer, the term of this patent is extended or adjusted under 35 U.S.C. 154(b) by 287 days.

(21) Appl. No.: 12/182,060

(22) Filed: Jul. 29, 2008

(51) Int. Cl.
*G01N 21/00* (2006.01)

(52) U.S. Cl. ............. 356/432; 324/754.21; 324/754.23; 372/38.1; 372/38.01

(58) Field of Classification Search .............. 356/432, 356/445, 446, 447; 372/29.02, 38.1, 38.01; 324/754.21, 754.23
See application file for complete search history.

(56) References Cited

U.S. PATENT DOCUMENTS

| | | | | |
|---|---|---|---|---|
| 4,237,427 A | * | 12/1980 | Holland | 372/29.02 |
| 4,795,260 A | * | 1/1989 | Schuur et al. | 356/400 |
| 5,074,669 A | * | 12/1991 | Opsal | 356/445 |
| 5,134,276 A | | 7/1992 | Hobbs | |
| 6,784,731 B2 | * | 8/2004 | Zhang | 330/149 |
| 7,130,055 B2 | * | 10/2006 | Borden et al. | 356/491 |
| 7,141,440 B2 | * | 11/2006 | Borden et al. | 438/5 |

OTHER PUBLICATIONS

Philip D. C. Hobbs, "Ultrasensitive Laser Measurement without Tears"—Applied Optics, vol. 36, No. 4, pp. 903-920, Feb. 1, 1997.

* cited by examiner

*Primary Examiner* — Tarifur R. Chowdhury
*Assistant Examiner* — Isiaka O Akanbi
(74) *Attorney, Agent, or Firm* — JDI Patent; Joshua D. Isenberg

(57) ABSTRACT

In a modulated optical reflectance (MOR) system, a laser noise suppression technique utilizes a reference beam split optically from a probe laser prior to injection of a beam from the probe laser into an MOR signal path. The reference beam and a probe beam reflected from the sample are sent to first and second detectors, which produce first and second signals. A signal combiner receives the second signal at a first input and produces a combiner signal that corresponds to a difference between signals applied to the first and a second input. A level balancer receives the first signal and a signal derived from the combiner signal and produces a balancer output that is coupled to the second input of the signal combiner. The combination of the balancer output and the second signal tends to cancel out an average value of the second signal from the combiner signal.

18 Claims, 4 Drawing Sheets

APPARATUS AND METHOD FOR NOISE REDUCTION IN MODULATED OPTICAL REFLECTANCE METROLOGY SYSTEM

TECHNICAL FIELD

Embodiments of the present invention relate generally to optical methods for inspecting and analyzing semiconductor wafers and other samples. In particular, embodiments of the present invention relate to noise suppression apparatus and methods for use in a modulated optical reflectance system to improve signal to noise ratio and to minimize undesirable laser noise.

BACKGROUND OF THE INVENTION

Modulated Optical Reflectance (MOR) measurement is often used for ion implant metrology. MOR technology utilizes an intensity modulated pump laser beam to create carrier plasma and thermal waves in a semiconductor sample. A second probe laser reflects from the excited area and the changes in optical reflectance coefficient caused by the propagating plasma and thermal waves are recorded as the MOR signal. Commercial systems utilizing this technology are used in monitoring the ion implantation process used in semiconductor manufacturing. Techniques that can improve the signal-to-noise ratio for these measurements increase the value of the measurements and extend the range of applications for metrology tools utilizing MOR technology.

Prior art systems using MOR for ion implant metrology have been limited in signal-to-noise ratio by probe laser noise, and specifically by laser intensity fluctuations with frequency content near the modulation frequency of the MOR technique. The MOR technique leads to a tiny amount of modulation riding on a relatively large DC probe laser beam. The ratio of signal level to DC, laser intensity is typically 1 part in $10^4$. Probe laser intensity fluctuations thus pose a significant obstacle to refining the precision and speed of MOR measurements. The probe beam fluctuations arise from various sources including interference and feedback phenomena interacting with the highly non-linear system of the laser cavity in which small perturbations can cause the energy of various cavity modes to fluctuate. Coupling between modes and the effects of temperature shifts can lead to "mode hopping", a term describing an unstable balance of energy between different cavity modes where laser output fluctuations are enhanced. A laser specification known as Relative Intensity Noise (RIN) is a measure of these fluctuations that are a fact of life in commercial lasers that are available for use in measurement systems. These fluctuations may be many times higher in intensity than the Schott noise limit for a probe laser of the same average intensity.

These fluctuations occur at frequencies that are typically too high for correction by the use of typical normalization and standardization techniques. Prior art methods of dealing with these fluctuations in MOR systems have included techniques for reducing laser noise fluctuations in the laser. One of these techniques uses modulation of the probe laser at a very high frequency compared to the pump modulation to stir the laser diode modes and thus improve laser diode noise. Active power stabilizers have also been used to reduce laser intensity fluctuations, but operating them at high enough bandwidths to significantly reduce the fluctuations near the MOR modulation frequency is expensive and technically challenging.

It is within this context that embodiments of the present invention arise.

SUMMARY OF THE INVENTION

Embodiments of the present invention provide an automatically balanced noise canceling detector for the probe laser to cancel the undesirable probe laser fluctuations at the point of detection rather than in the laser and thus to improve the signal-to-noise ratio for the MOR measurement system. A similar technique is described in detail in U.S. Pat. No. 5,134,276 as a useful technique for reducing noise in generalized laser measurement systems. However, such a technique has never been applied in an MOR system for the measurement of semiconductor wafer parameters.

According to an embodiment of the invention, in an MOR system, a comparison beam is split optically from a probe laser beam just after the output from a laser collimator and prior to injection of the collimated probe laser beam into the MOR signal path. This comparison beam is sent to a photodiode in the noise suppression apparatus. The reflected probe beam from the sample, which picked up modulation from the influence of the pump laser on the sample (MOR technique) is directed to a second photodiode in the apparatus. A low bandwidth control loop compares the two beams and adjusts a current divider to direct a fraction of the photocurrent from a comparison beam detector of the apparatus to cancel the average photocurrent from a signal detector. By so doing the high-frequency laser fluctuations can be directly subtracted at the input to the amplification electronics leaving only the uncancelled modulation signal, electronic noise, and the laser beam Schott noise. Since the noise of prior art systems was dominated by the probe laser fluctuations (even when laser noise reduction was applied), a large improvement in signal-to-noise ratio is obtained.

BRIEF DESCRIPTION OF THE DRAWINGS

Objects and advantages of the invention will become apparent upon reading the following detailed description and upon reference to the accompanying drawings in which.

DETAILED DESCRIPTION

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

An important motivating factor behind embodiments of the invention was the determination of the main source of noise in a modulated optical reflectance (MOR) system. As discussed above, in an MOR system a probe beam and a pump beam are applied to the same spot on a sample. The probe beam is reflected from a detector. The pump beam is modulated, which modulates the temperature T of the target. The reflectance r (the ratio of incident and reflected probe beam power) is a function of temperature T. However, the reflectance measurement is subject to various types and levels of noise. The dynamic of isolating types and levels of laser noise is complex and painstaking, requiring considerable empirical and theoretical study.

The noise factors examined were high frequency probe noise (H.F. probe), low frequency probe noise (L.F. probe), probe shot noise (Probe-shot), low frequency pump noise (L.F. pump), low frequency focus noise (L.F. focus), and low frequency separation (or beam pointing) noise (L.F. sep.).

A few experiments were suggested:
1) Quadruple the probe power, $I_p$ and assume the laser noise stays a constant percentage of the probe power.
2) Quadruple the pump power, $I_m$ and assume the noise stays as a constant percentage of the pump power.
3) Simply turn off the pump
4) Change separation between the probe and pump beams
5) Increase the focus offset Experiments were then performed following above-described considerations. For example, by observing the behavior of the standard deviation of the detected thermal wave signal TW as a function of probe power it was determined that the noise scales with the probe power. In addition, the standard deviation of the thermal wave signal TW did not drop dramatically if the pump beam was turned off. These observations indicated that the problem was high-frequency probe noise—at least within the assumptions of the noise terms being limited to pump shot, pump amplitude, probe shot, probe amplitude, constant electronic, beam motion, or focus.

Figure 1:
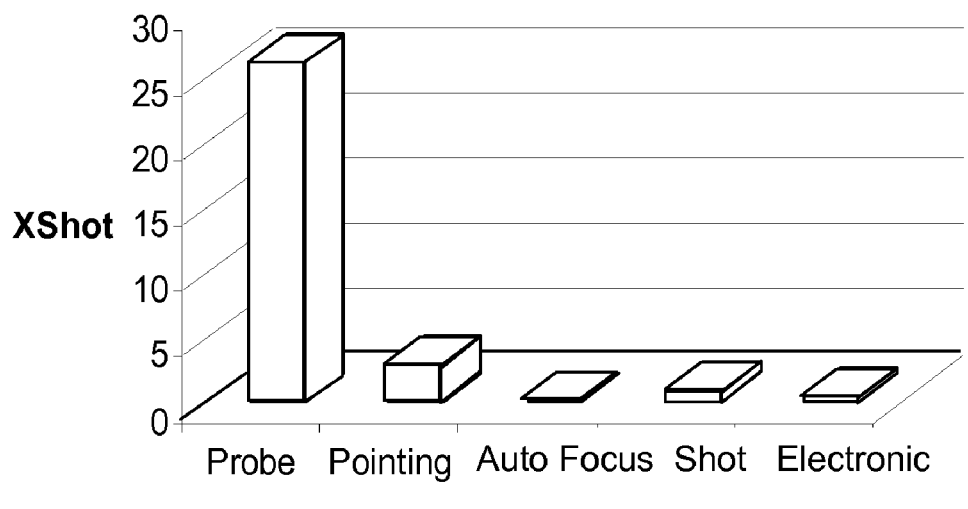
FIG. 1 is a graphical representation of the types and levels of signal noise generated by an MOR system.

FIG. 1 is a graphical representation of the types and levels of noise evaluated during experimentation, indicating the substantial difference between probe laser noise and the other types of noise evaluated. The graph shows almost a 10 to 1 ratio between probe laser noise and the next highest source of laser noise.

Following a determination that probe laser noise was the primary source of noise in the MOR system, a noise suppression apparatus was developed for incorporation into an MOR system. Embodiments of the present invention relate to apparatus and methods for noise reduction in modulated optical reflectance metrology system.

According to an embodiment of the present invention a laser noise suppression apparatus for a modulated optical reflectance (MOR) system may include a pump laser, a probe laser and a beam splitter. The pump laser is configured to generate a modulated beam that is directed at a surface portion of a sample to excite the surface portion. The probe laser is configured to generate a non-modulated beam. The beam splitter is configured to split the non-modulated beam into first and second portions.

Such laser noise suppression apparatus may further include first and second detectors and a signal combiner. The first detector is configured to receive the first portion of the non-modulated probe laser beam and produce a first signal corresponding to the first portion. The second detector is configured to receive a reflected part of the second portion of the non-modulated probe laser beam that has been reflected from said surface portion. The second detector is further configured to produce a second signal corresponding to the reflected part of the second portion. The signal combiner has first and second inputs and an output. The first input is configured to receive the second signal, and the signal combiner is configured to produce a combiner signal at the output that corresponds to a difference between signals applied to the first and second inputs.

A level balancer is configured to receive as inputs the first signal and a signal derived from the combiner signal and to produce a balancer output that is coupled to the second input of the signal combiner. The level balancer and signal combiner are configured such that combination of the balancer output and the second signal tends to cancel out an average value of the second signal from the combiner signal.

Figure 2:
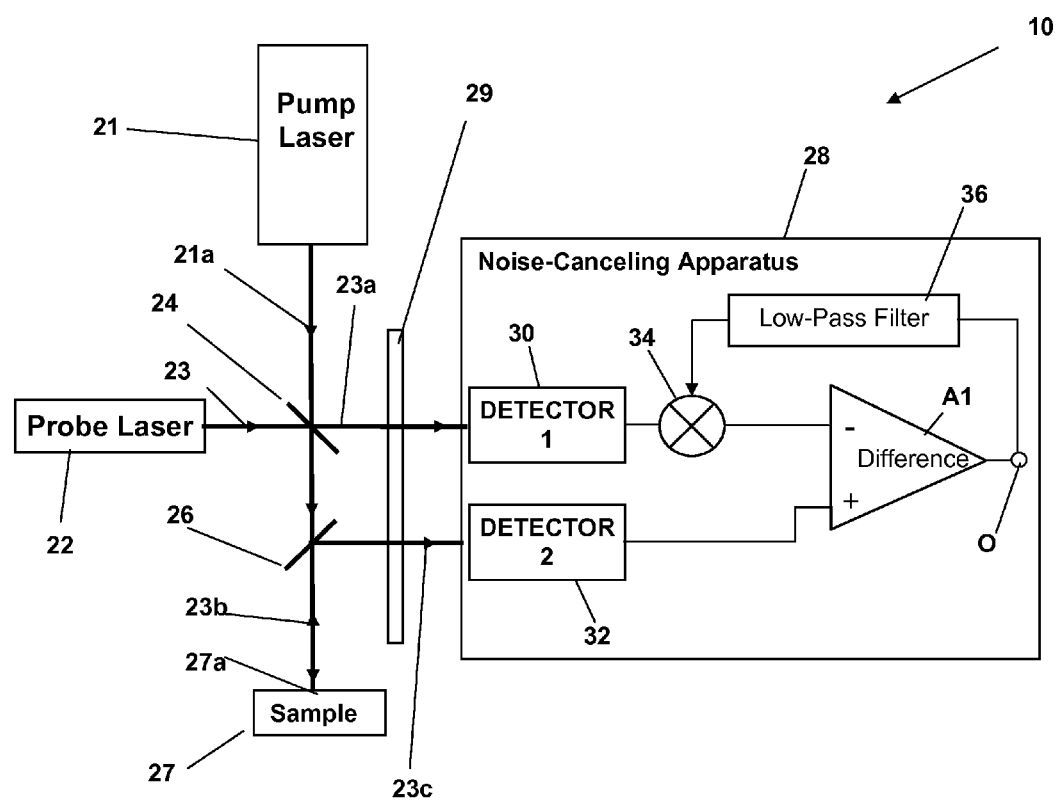
FIG. 2 is a diagram, partially in schematic, of a Modulated Optical Reflectance (MOR) system incorporating noise suppression apparatus in accordance with a preferred embodiment of the present invention.

By way of example, and without loss of generality, a Modulated Optical Reflectance (MOR) system incorporating noise suppression apparatus in accordance with a preferred embodiment of the present invention is shown, partially in schematic, in the diagram of FIG. 2. The MOR system 10 comprises a pump laser 21, a probe laser 22, beam splitters 24 and 26 and noise canceling apparatus 28, for processing a sample 27. By way of example, the sample 27 may be a semiconductor wafer and the MOR system 10 is measuring the doping characteristics of the wafer surface after processing.

The noise canceling apparatus 28 includes a probe comparison beam detector 30, a probe signal beam detector 32, a signal level balancer 34, and a combiner, e.g., a differential amplifier A1 having a non-inverting input (+), an inverting input (−) and an output O. The output of the differential amplifier A1 is a combined signal that corresponds to a difference between the signals applied to its two inputs. A feedback loop between the output of the amplifier A1 and the level balancer 34 includes a low pass filter 36.

The MOR system 10 operates as follows. The pump laser 21 is activated to deliver a modulated excitation beam 21a, typically in the 1 MHz range, to the surface of the sample 27. The excitation beam 21a travels through beam splitters 24 and 26 to impinge on an upper surface 27a of the sample 27.

The probe laser 22 generates an unmodulated probe beam 23 that is delivered to the beam splitter 24. A first portion 23a of the probe beam 23 is transmitted through the beam splitter 24 to the noise suppression apparatus 28 and a second portion 23b of the probe beam 23 is directed by the beam splitter 24 to the upper surface 27a of the sample 27. A reflected portion 23c of the second portion probe beam 23 is directed by the beam splitter 26 from the surface 27a to the noise suppression apparatus 28. A blocking filter 29 blocks any part of the pump beam 21a directed to the noise suppression apparatus 28 by the beam splitter 24 and transmits the first portion 23a of the unmodulated probe beam 23 passing through the beam splitter 24 to the noise suppression apparatus 28. The reflected portion 23c of the probe beam 23 also passes through the blocking filter 29 before reaching the noise suppression apparatus 28.

Within the noise suppression apparatus 28, a probe comparison beam detector 30 receives the first portion 23a of the probe beam 23 and processes such input probe beam to produce a first signal corresponding to the first portion 23a. A second detector, probe signal beam detector 32, receives the reflected portion 23c of the probe beam 23 and processes such reflected portion 23c to produce a second signal corresponding to the reflected portion 23c. The amplifier A1 receives the second signal from the signal beam detector 32 at its non-inverting input (+). The first signal from the probe comparison beam detector 30 is sent to a level balancer 34 where it is combined with a feedback signal from the output O of amplifier A1 that has been passed through the low pass filter 36. The output from the level balancer 34 is then applied to the inverting input (−) of the amplifier A1. The system 28 is so configured that the amplifier A1 additively combines the second signal and the balancer output in a sense which tends to cancel a steady-state current and undesirable noise signals from the second signal to produce an output signal representing an information component of the second signal.

Figure 3:
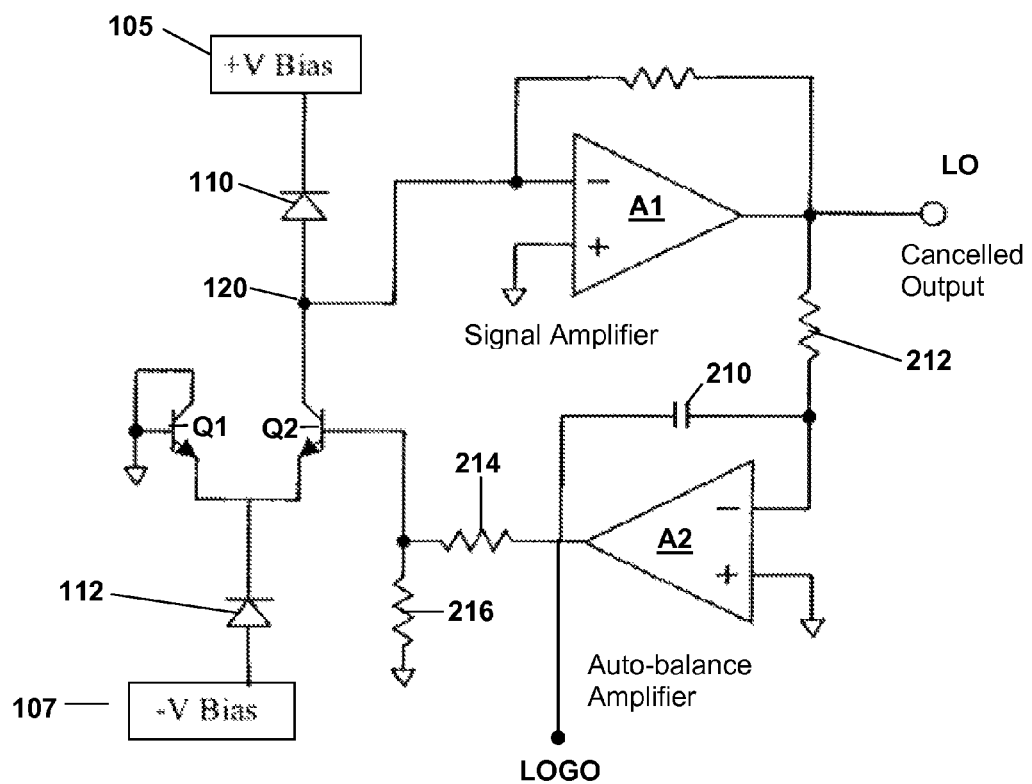
FIG. 3 is a schematic diagram of a preferred form of a noise suppression circuit incorporated in the MOR system of the preferred embodiment.

FIG. 3 is a schematic diagram, partly in block diagram form of an example of detection circuitry which may be used in the noise suppression apparatus 28, shown in FIG. 2. In this example of a detector, a signal photodiode 110 and a sample photodiode 112 may be activated by the respective reflected probe beam 23c and comparison probe beam 23a to pass current provided by the operational power sources 105 and 107, respectively. The photocurrent passed by the photodiode 110, less the collector current $I_{C2}$ of transistor Q2, may then be applied to a summing junction 120 of a conventional operational amplifier A1. The amplifier A1 converts the net current at its summing junction to a voltage signal LO, which serves as a linear output signal of the apparatus 28.

The operational potentials provided by the respective operational power sources 105 and 107 depend on the type of photodetectors used. By way of example, the photodetectors 110 and 112 may be silicon pin diodes and the operational powers sources 105 and 107 may provide +15 volts and −15 volts, respectively.

The sample photocurrent passed by the photodiode 112 is applied to joined emitter electrodes of a pair of bipolar transistors, Q1 and Q2, which are configured as a differential pair. In the embodiment shown in FIG. 3, the transistors Q1 and Q2 may be fast, matched transistors having current gain-bandwidth products ($f_T$) of approximately 5 GHZ. The collector and base electrodes of the transistor Q1 are coupled to a source of reference potential (e.g. ground), the base electrode of transistor Q2 is coupled to the output of servo-amplifier A2.

Although bipolar transistors are used in the example described above, it is contemplated that other types of variable conductive devices, such as field effect transistors may be used in a similar configuration to perform the current division operation.

In operation, a portion, $I_{C2}$, of the sample photocurrent is passed by the transistor Q2 to the summing junction 120 while the remainder of the sample photocurrent, $I_{C2}$, is shunted to ground through Q1 in response to a feedback circuit. As set forth above, the optical system is configured so that the reference beam is stronger than the probe beam. Thus, the reference photocurrent is always greater than the probe photocurrent. Thus, the magnitude of the DC component of the current $I_{C2}$ is controlled to be substantially equal in magnitude to the DC component of the probe photocurrent by shunting the excess reflected photocurrent to ground.

Using the Ebers-Moll model of the two bipolar transistors Q1 and Q2, the respective collector currents passed by the transistors, $I_{C1}$ and $I_{C2}$ may be defined by the equation (1)

$$\frac{I_{C1}}{I_{C2}} = \exp\frac{q\Delta V_{BE}}{kT} \quad (1)$$

where q is the electron charge, T is absolute temperature and k is Boltzmann's constant. Thus, by varying $\Delta V_{BE}$, the portion of the sample photocurrent that is passed to the summing junction 120 of the amplifier A1 can be controlled electronically.

By controlling the DC component of the sample photocurrent applied to the summing junction 120, the circuitry shown in FIG. 3 ensures that the noise components and the direct current components of the laser beam are cancelled in the output signal LO. As set forth above, however, the shot noise components of the photocurrents are uncorrelated and combine additively in power in the signal LO. Thus, the noise floor of the signal LO is limited to approximately 3 dB above the shot noise level of the signal photocurrent. The bandwidth of the signal LO, however, is limited by the bandwidth of the amplifier A1. For optimum performance, it is desirable to select an amplifier A1 which has a relatively wide bandwidth and which adds only a small amount of noise to the signals it amplifies.

Since the collector currents of the transistors Q1 and Q2 are exponential functions of the voltage $V_{BE}$, the transconductances of the transistors Q1 and Q2 are proportional to their collector currents. Consequently, any fluctuation in the reflected photocurrent is subdivided in substantially the same ratio as the DC component. Thus, by canceling the DC components of the photocurrents, all variations in the probe and reflected photocurrents which are related to excess noise components of the incident laser beams are also cancelled.

A feedback loop controls the current division performed by the transistors Q1 and Q2 to ensure substantial cancellation of the DC component of the probe photocurrent and, thus, the noise components as well.

While not shown here, it may be desirable to insert a so-called cascode transistor to isolate the summing junction 120 of the transresistance amplifier A1 from the capacitance of the photodiode 110, which, as is well known, may cause noise gain peaking or instability in the amplifier A1.

The feedback loop provided in the circuitry shown in FIG. 3 includes a resistor 212, a capacitor 210 and an integrating servo amplifier A2. The frequency bandwidth of the feedback loop is approximately 100 Hz. This frequency bandwidth is determined by the values of the resistor 212 and capacitor 210 and by the gain of the feedback loop as reduced by the voltage divider network formed by the resistors 214 and 216. It has been determined that this bandwidth is sufficient in many cases to track the relatively low frequency drifts in the probe photocurrent which affect the DC component of the difference signal. It is contemplated, however, that by choosing different component values for the capacitor 210 and the resistors 212, 214 and 216, this bandwidth may be made narrower or considerably wider if desired.

In the circuit configuration shown in FIG. 3, the portion of the reference photocurrent passed by the transistor Q2 is sufficient to substantially cancel all but the shot noise components of the two photocurrents. This circuit is effective out to very high frequencies regardless of the bandwidth of the feedback loop since, as set forth above, the relative instantaneous noise fluctuations of the reference and probe photocurrents are essentially exactly proportional to their DC levels. The cancellation bandwidth limit is determined by the unity gain frequencies ($f_T$) of the transistors Q1 and Q2.

As an added benefit, the $\Delta V_{BE}$ for the transistors Q1 and Q2, provides an alternative output signal from the noise apparatus 28. In the circuitry shown in FIG. 3, this signal is proportional to the base voltage of the transistor Q2 as referenced to ground. The output signal LOGO, available at the output terminal of the servo amplifier A2, is proportional to the $V_{BE}$ of the transistors Q1 and Q2. LOGO is proportional to $\Delta V_{BE}$ as the ratio of the sum of the values of resistors 214 and 216 to the value of resistor 216.

Since LOGO is related to the ratio of the reference current to the probe current then, by the Ebers-Moll equation, LOGO can be described by equation (2)

$$LOGO = \frac{R_{214} + R_{216}}{R_{216}} \frac{kT}{q} \ln\left(\frac{I_{reference}}{I_{probe}} - 1\right) \quad (2)$$

If this signal is used as the output signal of the apparatus 28, then the performance of the apparatus 28 is much like that of divider noise canceling circuits, in which the intermodulation noise of the probe current is suppressed in the signal LOGO, since the amplitude of LOGO depends only on the ratio of the probe photocurrent ($I_{probe}$) to the reference photocurrent ($I_{reference}$).

An important feature of the LOGO output signal is that, unlike the output of a divider circuit, the level of noise in the signal LOGO does not increase as the loop bandwidth is approached, since the DC cancellation effectively guarantees the cancellation of additive noise at all frequencies of interest. Instead, only the suppression of noise intermodulation decreases. In a conventional divider circuit, by contrast, the level of excess noise in the output signal increases with frequency out to the bandwidth of the feedback loop.

Since the bandwidth of the LOGO output signal is limited by the bandwidth of the feedback loop, it may be desirable to decrease the time constant of the integrating servo amplifier A2 by decreasing the value of the capacitor 210, the value of the resistor 212 or both.

Although the transistors Q1 and Q2 are described as matched transistors, unmatched transistors may also be used if strict temperature stability of the output signal LOGO is not required.

Figure 4:
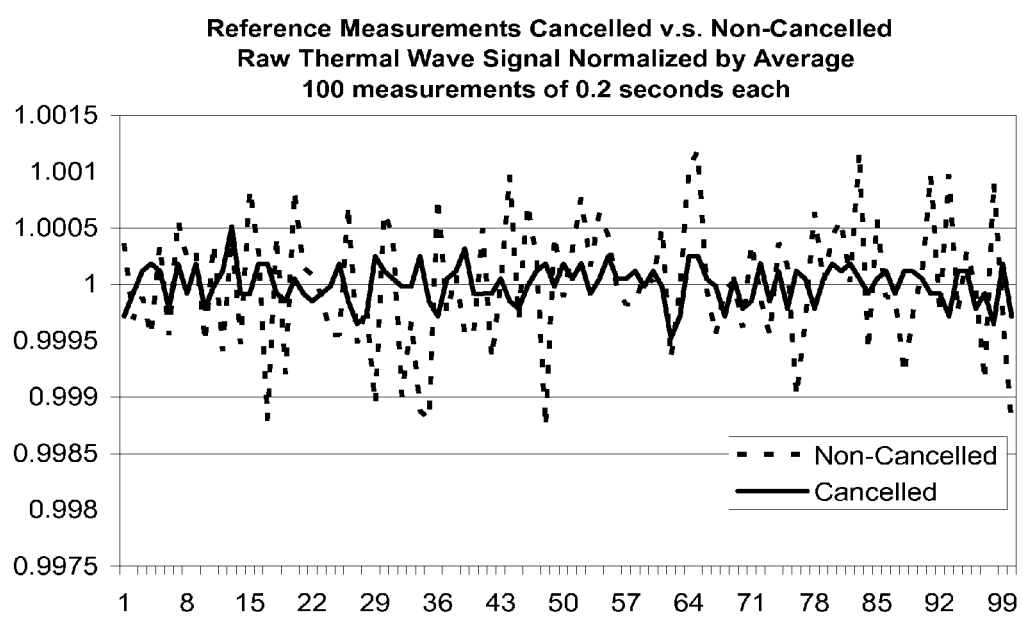
FIG. 4 is a diagram comparing a raw thermal wave signal not processed by an MOR system having noise suppression circuitry with a raw thermal wave signal processed by an MOR system having noise suppression circuitry.

FIG. 4 shows that substantial improvement has been achieved with the noise suppression apparatus of the present invention. In fact, when the cancelled noise levels are compared to the non-cancelled noise levels, a 3× signal/noise improvement on MOR measurements is seen. Improvements of greater than 10× have been observed in some cases.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. Laser noise suppression apparatus for a modulated optical reflectance (MOR) system including a pump laser configured to generate a modulated beam that is directed at a surface portion of a sample for exciting said surface portion, a probe laser configured to generate a non-modulated beam, and a beam splitter configured to split the non-modulated beam into a first portion and a second portion, said laser noise suppression apparatus including:
   a first detector configured to receive the first portion of the non-modulated probe laser beam to produce a first signal corresponding to the first portion;
   a second detector configured to receive a reflected part of the second portion of the non-modulated probe laser beam that has been reflected from said surface portion, wherein the second detector is configured to produce a second signal corresponding to the reflected part of the second portion;
   a signal combiner having first and second inputs and an output, wherein the first input is configured to receive the second signal, wherein the signal combiner is configured to produce a combiner signal at the output that corresponds to a difference between signals applied to the first and second inputs,
   a level balancer configured to receive as inputs the first signal and a signal derived from the combiner signal and produce a balancer output that is coupled to the second input of the signal combiner,
   wherein the level balancer and signal combiner are configured such that combination of the balancer output and the second signal tends to cancel out an average value of the second signal from the combiner signal.

2. The laser noise suppression apparatus of claim 1 wherein the signal combiner is configured to additively combine said second signal and the level balancer output in a sense which tends to cancel a steady-state current and undesirable noise signals from said second signal to produce an output signal representing an information component of said second signal.

3. The laser noise suppression apparatus of claim 1 wherein the level balancer includes a signal divider configured to receive the first signal and subdivide the first signal into first and second component signals having a ratio that is determined by an output of a low-pass filter coupled between the output of the signal combiner and an input of the level balancer.

4. The laser noise suppression apparatus of claim 3, wherein:
   said signal divider includes first and second variable conduction devices, each having first and second electrodes that define a principal conduction path and a third electrode for applying a signal to control the conductivity of the principal conduction path;
   wherein the respective first electrodes of said first and second variable conduction devices are coupled to receive the one of the first and second signals having the larger steady-state current component;
   wherein the second electrode of said first variable conduction device is coupled to a source of reference potential; and
   wherein the second electrode of said second variable conduction device is coupled to said signal combiner.

5. The laser noise suppression apparatus of claim 4 wherein said first and second variable conduction devices are bipolar transistors.

6. The laser noise suppression apparatus of claim 1, further including:
   a feedback device coupled to receive the combiner signal and produce the signal derived from the combiner signal, wherein the signal produced from the combiner signal, wherein the feedback device, level balancer and signal combiner are configured such that the combiner signal has a steady-state value that is approximately equal to zero.

7. The laser noise suppression apparatus of claim 6 wherein said feedback device includes an integrating servo amplifier.

8. In a laser noise suppression method for a modulated optical reflectance (MOR) system, comprising:
   generating a modulated laser beam that is directed at a surface portion of a sample, generating a non-modulated laser beam,
   splitting the non-modulated probe laser beam into a first portion and a second portion;

producing a first signal corresponding to the first portion of the non-modulated beam;

reflecting the second portion of the non-modulated beam from the surface portion;

producing a second signal corresponding to a reflected part of the second portion of the non-modulated beam;

additively combining a portion of the first signal with the second signal to produce a combined output, wherein an average value of the second signal is canceled out from the combined signal.

9. The method of claim 8 wherein the portion of the first signal is determined from a signal derived from the combined output signal.

10. The method of claim 9 wherein the signal derived from the combined output corresponds to a difference between the first and second signals.

11. The method of claim 8 wherein additively combining the portion of the first signal with the second signal includes combining the portion of the first signal with the second signal in a sense that tends to cancel a steady-state current and undesirable noise signals from said second signal so that the combined signal represents an information component of said reflected portion of the non-modulated probe laser signal.

12. The method of claim 8, wherein additively combining a portion of the first signal with the second signal includes:

feeding back a portion of the combined output to control the portion of the first signal that is combined with the second signal in such a way that said combined output is approximately equal to zero.

13. The method of claim 12 wherein feeding back the portion of the combined output includes low-pass filtering the portion of the combined output.

14. Laser noise suppression apparatus for a modulated optical reflectance (MOR) system including a pump laser configured to generate a modulated optical signal that is directed at a surface portion of a sample, a probe laser configured to generate a non-modulated signal, and a beam splitter directing a first portion of the non-modulated probe laser signal into the noise suppression apparatus and a second portion of the non-modulated probe laser signal at the surface portion of the sample, said laser noise suppression apparatus including:

a detector configured to receive the first portion of the non-modulated probe laser signal and a part of the second portion that has been reflected from the surface portion of the sample, wherein the detector is configured to produce a first current signal corresponding to the first portion and a second current signal corresponding to the reflected part of the second portion;

signal dividing means coupled to the detector to receive the first current signal and subdivide the first current signal into first and second component current signals, according to a ratio that is determined by a control signal; and combining means for additively combining said first current signal and the second current signal in a sense which tends to cancel the steady-state current and probe laser fluctuation noise signals from said part of the second portion that has been reflected from the surface to produce an output signal representing an information component of said reflected portion of the non-modulated probe laser signal.

15. The laser noise suppression apparatus of claim 14, wherein:

said dividing means includes first and second variable conduction devices, each having first and second electrodes that define a principal conduction path and a third electrode adapted to receive a signal to control a conductivity of the principal conduction path;

and wherein the respective first electrodes of said first and second variable conduction devices are coupled to receive the one of the first and second current signals having the larger steady-state current component;

and wherein the second electrode of said first variable conduction device is coupled to a source of reference potential; and the second electrode of said second variable conduction device is coupled to said combining means.

16. The laser noise suppression apparatus of claim 15 wherein said first and second variable conduction devices are bipolar transistors.

17. The laser noise suppression apparatus of claim 14, further including:

feedback means, coupled to receive the output signal of the combining means, for controlling the signal dividing means to produce a first component current signal which, when combined with the one of the first and second current signals having the smaller steady-state current component signal produces said output signal having a steady-state current that is approximately equal to zero.

18. The laser noise suppression apparatus of claim 17 wherein said feedback means includes integrating servo amplifier means.

* * * * *